(12) United States Patent
Lam et al.

(10) Patent No.: US 12,037,631 B2
(45) Date of Patent: Jul. 16, 2024

(54) SYSTEM AND METHOD FOR DETECTING A TARGET ENZYME

(71) Applicant: City University of Hong Kong, Kowloon (HK)

(72) Inventors: Hon-Wah Lam, New Territories (HK); Chuanwen Zhou, Kowloon (HK); Yun-Wah Lam, Kowloon (HK)

(73) Assignee: City University of Hong Kong, Kowloon (HK)

( * ) Notice: Subject to any disclaimer, the term of this patent is extended or adjusted under 35 U.S.C. 154(b) by 750 days.

(21) Appl. No.: 17/063,810

(22) Filed: Oct. 6, 2020

(65) Prior Publication Data
US 2022/0106621 A1    Apr. 7, 2022

(51) Int. Cl.
*C12Q 1/37* (2006.01)
*C12Q 1/28* (2006.01)
*C12Q 1/527* (2006.01)

(52) U.S. Cl.
CPC .............. *C12Q 1/37* (2013.01); *C12Q 1/28* (2013.01); *C12Q 1/527* (2013.01); *C12Q 2326/12* (2013.01)

(58) Field of Classification Search
None
See application file for complete search history.

(56) References Cited

U.S. PATENT DOCUMENTS

| | | | | |
|---|---|---|---|---|
| 4,463,090 A | * | 7/1984 | Harris | G01N 33/586 436/829 |
| 7,803,572 B2 | | 9/2010 | Braven et al. | |
| 8,017,151 B2 | * | 9/2011 | Batrakova | A61K 31/765 424/78.37 |
| 2014/0024106 A1 | * | 1/2014 | Cullen | A61L 15/225 435/287.9 |
| 2019/0328833 A1 | * | 10/2019 | Ferguson | A61K 38/12 |

FOREIGN PATENT DOCUMENTS

| | | |
|---|---|---|
| CN | 104049007 | 9/2014 |
| CN | 107064505 | 8/2017 |
| EP | 0144744 | 6/1985 |

* cited by examiner

*Primary Examiner* — Robert J Yamasaki
(74) *Attorney, Agent, or Firm* — Renner, Kenner, Greive, Bobak, Taylor & Weber

(57) ABSTRACT

The present invention relates to a system for detecting a target enzyme in a sample, the system including a substrate, a first enzyme immobilized on the substrate via a first linker, and a second enzyme immobilized on the substrate via a second linker, wherein the first linker is cleavable by the target enzyme or the second enzyme to release the first enzyme for cleaving the second linker, thereby releasing the second enzyme; and a method for detecting a target enzyme in a sample including applying the sample to said system.

21 Claims, 6 Drawing Sheets
Specification includes a Sequence Listing.

SYSTEM AND METHOD FOR DETECTING A TARGET ENZYME

TECHNICAL FIELD

The invention relates to a system and a method for detecting a target enzyme and particularly, although not exclusively, a protease in a sample.

SEQUENCE LISTING

The Sequence Listing file entitled "sequencelisting" having a size of 439 bytes and a creation date of Oct. 6, 2020 that was filed with the patent application is incorporated herein by reference in its entirety.

BACKGROUND

Enzymes are vital for life and are involved in various important functions in the body and chemical reactions. Among various types of enzymes, proteases play a pivotal role in regulating important physiological processes and some of them further act as biomarkers for diseases diagnosis or foodborne pathogens detection. For example, extracellular proteases are associated with cancer-cell proliferation and are also targets for the detection of foodborne pathogens like *Straphylococcus aureus, Escherichia coli* and *Salmonella* sp. However, extracellular proteases are generally present in trace amount and therefore it is difficult to detect them precisely.

Recently, there are developed self-amplification approaches in the chemosensing/biosensing researches. Most of the current approaches involve zymography, cascaded enzymatic reactions and/or the use of DNA aptamers. However, these approaches are usually time-consuming, tedious and require laborious design of cascaded biochemical pathways.

Accordingly, there is still a need to develop a new and effective approach to detect or determine the identity and the amount of an enzyme such as a protease secreted from a microorganism for diagnosis or food test.

SUMMARY OF THE INVENTION

It is an object of the invention to address the above needs, to overcome or substantially ameliorate the above disadvantages or, more generally, to provide a system or a kit capable of detecting the presence or amount of an enzyme of interest such as a protease, preferably an extracellular protease, in a sample.

In accordance with a first aspect of the invention, there is provided a system for detecting a target enzyme in a sample, the system comprising a substrate, a first enzyme immobilized on the substrate via a first linker, and a second enzyme immobilized on the substrate via a second linker, wherein the first linker is cleavable by the target enzyme or the second enzyme to release the first enzyme for cleaving the second linker, thereby releasing the second enzyme.

In accordance with a second aspect of the invention, there is provided a method for detecting a target enzyme in a sample comprising applying the sample to a system, the system comprising a substrate, a first enzyme immobilized on the substrate via a first linker, and a second enzyme immobilized on the substrate via a second linker, wherein the first linker is cleavable by the target enzyme or the second enzyme to release the first enzyme for cleaving the second linker, thereby releasing the second enzyme.

The inventors have developed an effective system and method to detect an enzyme particularly an extracellular protease based on an autocatalytic mechanism. The present invention herein is suitable for detection of collagenase which is a common extracellular protease found in most bacteria cultures, and is also suitable for other extracellular proteases including those present in trace amount in a sample. The present invention is particularly useful in clinical diagnosis, researches and food safety surveillance.

BRIEF DESCRIPTION OF THE DRAWINGS

Embodiments of the invention will now be described, by way of example, with reference to the accompanying drawings in which.

DETAILED DESCRIPTION OF THE PREFERRED EMBODIMENT

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. Other than in the working examples, or where otherwise indicated, all numbers used herein should be understood as modified in all instances by the term "about". The term "about" when used in connection with a number can mean, for example, ±2%.

In one aspect, the present invention pertains to a system for detecting a target enzyme in a sample in an autocatalytic amplification manner. The system contains at least two enzymes immobilized on a surface of a substrate. The enzymes are immobilized on the substrate via different linkers which are cleavable by the corresponding enzyme and one of the linkers is cleavable by the target enzyme to trigger a chain reaction. The signal given by the target enzyme will be subsequently amplified for quantitative determination.

The system preferably includes a substrate, a first enzyme immobilized on the substrate via a first linker, and a second enzyme immobilized on the substrate via a second linker, wherein the first linker is cleavable by the target enzyme or the second enzyme to release the first enzyme for cleaving the second linker, thereby releasing the second enzyme.

Figure 1:
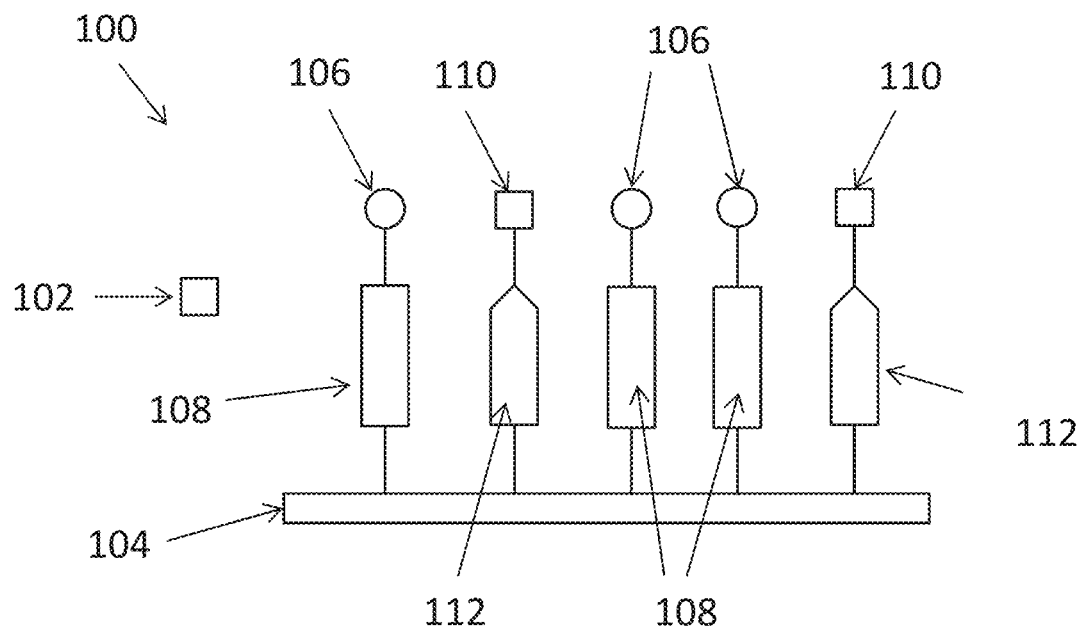
FIG. 1 is a diagram showing a system of an embodiment of the present invention.

With reference to FIG. 1, there is provided a diagram showing an embodiment of a system 100 for detecting a target enzyme 102 in a sample. The system is applicable for detection of the presence or amount of the target enzyme, or the activity of the target enzyme in the sample. The target enzyme 102 can be any enzyme of interest including, but not limited to, a protease, a lipase, a nuclease, a glycoside hydrolase, and an amidase. In an embodiment, the target enzyme 102 is a protease particularly an extracellular protease. The extracellular protease may be a collagenase for example a collagenase secreted by a microorganism.

The sample may be obtained from a plant, a mammal such as an animal or a human, or a food product such as a dairy product. In an embodiment, the sample is obtained from a spoiled food or a food product that is susceptible to bacterial contamination.

Alternatively, the sample may be obtained from an individual suffering from an infection or being susceptible to an infection caused by a microorganism including, but not limited to, a bacterium, a virus, a fungus, and a protozoa. The sample may be a biological sample selected from the group consisting of whole blood, plasma, serum, urine, cerebrospinal fluid, a cell culture, and bone marrow. In one embodiment, the sample is plasma, i.e. a cell-free sample, obtained from an individual suffering from or being susceptible to an infection. In another embodiment, the sample may be a cell or tissue culture.

Figure 2:
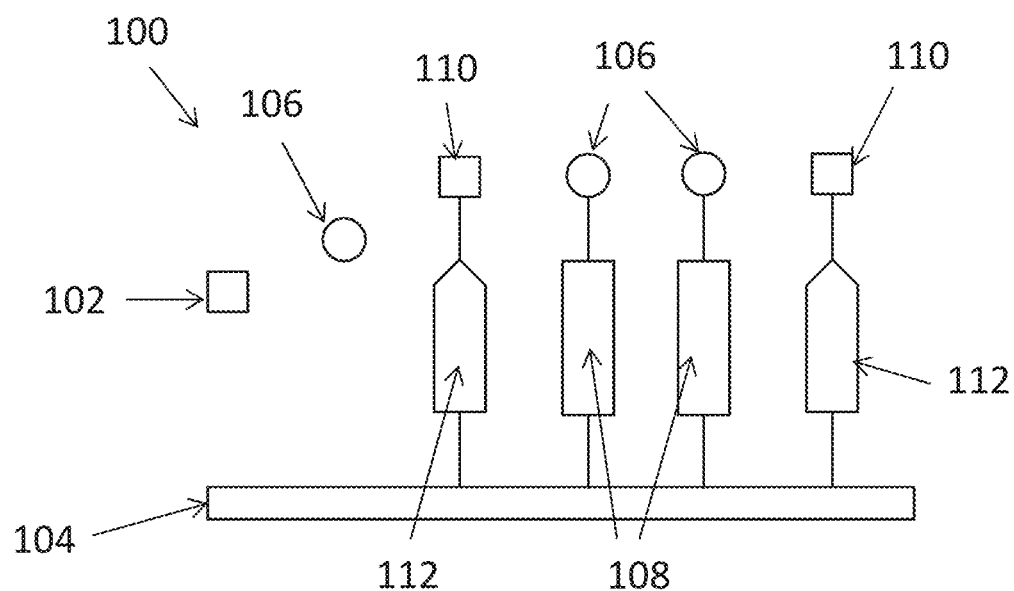
FIG. 2 is a diagram showing the release of a first enzyme after the cleavage of the first linker in the embodiment of FIG. 1.

Referring to FIGS. 1 and 2, the system 100 includes a substrate 104, a first enzyme 106 immobilized on the surface of the substrate 104 via a first linker 108, and a second enzyme 110 immobilized on the surface of the substrate 104 via a second linker 112. The immobilized first and second enzymes 106, 110 are bound and only become free to perform an enzymatic reaction when they are released from the substrate 104. The first enzyme 106 and the second enzyme 110 are different. In an embodiment, the first enzyme 106 is an alginase, i.e an alginate lyase, and the second enzyme 110 is a protease for example collagenase.

The substrate 104 may be any solid object or particle that can provide a platform for attaching one or more enzymes thereon, and provide sufficient space for the enzymes to perform their respective enzymatic reaction. The substrate 104 may include or made from glass, ceramic, metal and/or alloy. For example, the substrate may be a glass slide, a ceramic plate, a metal chip, a cell plate or a microplate containing multiple wells. In an embodiment, the substrate 104 has a certain depth to receive the sample for facilitating the enzymatic reactions.

In an embodiment, the substrate 104 is pretreated to have a binding group exposed on its surface for coupling with the first or second linker 108, 112 so as to hold the respective enzyme 106, 110 firmly on the surface. The binding group may include an amino group, an oligomer, or a polymer which is capable of forming a covalent bond with the first and second linker 108, 112. In a particular embodiment where the substrate 104 is a glass substrate and the binding group is an amino group, the substrate 104 is sonicated in a piranha solution, e.g. a mixture of concentrated sulfuric acid $H_2SO_4$ and 30% hydrogen peroxide $H_2O_2$ at a volume ratio of 7:3, and γ-amino-propyl-trimethoxy silane (APTES) for a period of time. The resultant substrate 104 thus carries amino groups on its surface. Advantageously, the binding group helps to immobilize the first and second linker 108, 112 and their corresponding enzymes 106, 110 on the substrate 104 stably before the sample is introduced onto the substrate 104.

In the presence of the binding group, the first linker 108 and the second linker 112 can be coupled to the substrate 104 in an efficient manner. The respective first and second enzyme 106, 110 are subsequently coupled to the linkers 108, 112 for example via Schiff base linkages.

Each of the first and second linker 108, 112 includes or consists of a peptide, a polysaccharide or a polymer, with one end being coupled to the substrate optionally via a binding group, and another end being coupled to the respective first or second enzyme 106, 110. Preferably, the first and second linker 108, 112 contains cleavage sites cleavable by the corresponding enzyme.

In an embodiment, the first linker 108 includes a peptide providing a cleavage site for a target enzyme. When the target enzyme is a protease particularly a collagenase, the first linker 108 may include an amino acid sequence of GGGLGPAGGK (SEQ ID NO: 1) which provides a cleavage site between leucine (L) and glycine (G). First linker 108 can be artificially synthesized according to the target enzyme or prepared from a naturally occurring molecule. When the target enzyme 102 in the sample comes into contact with the first linker 108, it binds and cleaves the first linker 108 at the cleavage site to release the associated first enzyme 106 from the substrate. The first enzyme 106 in free form is capable of binding and cleaving the second linker 112.

The second linker 112 is configured to be cleaved by the first enzyme 106 so as to release the associated second enzyme 110. The structure of the second linker 112 basically depends on the first enzyme 106, and may include an amino acid sequence, and/or a polymer such as a polysaccharide. In an embodiment, the second linker 112 includes a polysaccharide having a cleavage site cleavable by the first enzyme 106. For instance, the second linker 112 includes an alginate moiety when the first enzyme 106 is an alginate lyase. In an embodiment where the first enzyme 106 is a protease enzyme instead of alginate lyase, both the first and second linkers 108, 112 contain a peptide segment acting as a target substrate for the protease enzyme immobolized on the respestive first or second linkers 108, 112. That is, the first linker 108 contains a peptide with an amino acid sequence that can be specifically cleaved by the second enzyme 110. Similarly, the second linker 112 contains a peptide with an amino acid sequence that can be specifically cleaved by the first enzyme 106.

The second enzyme 110 has a structure substantially identical or identical to the target enzyme 102. In an embodiment where the target enzyme 102 is collagenase, the second enzyme 110 is collagenase or a derivative of collagenase. The released second enzyme 110 then binds and cleaves the first linker 108 together with the target enzyme 102, thereby continuously triggering the enzymatic reaction on the substrate to release more enzymes for detection at a later stage.

Preferably, the first enzyme 106 and the second enzyme 110 are immobilized on the substrate 104 at a pre-set amount. For example, the ratio of the first enzyme 106 to the second enzyme 110 is from 1:3 to 3:1, from 1:2 to 2:1, or about 1:1. Advantageously, the set amount of the second enzyme 110 is sufficient to enable the later indirect or direct measurement of the presence or amount of the target enzyme 102 even if the target enzyme 102 is present in trace amount in the sample.

In a particular embodiment where the first enzyme 106 is an alginate lyase and the second enzymes 110 is a protease particularly a collagenase, the immobilization of the first and second enzymes 106, 110 on the substrate 104 may involve the following steps. The area on the pretreated substrate 104 designated for the immobilization of the first linkers 108 and first enzyme 106 is covered with a PEG-aldehyde solution (obtained from PEG-400 and acetic anhydride in DMSO) in a buffer of pH 8.4, followed subsequently by a solution of the linker 108 in Tris-HCl buffer of pH 8.4, a solution of peptide having an amino acid sequence of GGGLGPAGGK (SEQ ID NO:1) which provides a cleavage site between leucine (L) and glycine (G) for the target enzyme 102 which is a protease particularly a collagenase, a solution of PEG-aldehyde solution in a Tris-HCl buffer of pH 8.4, and a solution of the first enzyme 106 in PBS buffer of pH 7.4. Unbound enzymes are washed away by PBS buffer of pH 7.4 and the area is treated with a sodium cyanoborohydride solution. Next, the area on the pretreated substrate 104 designated for the binding of the second linker 112 and the second enzyme 110 is covered by an oxidized sodium alginate solution (obtained from the reaction between sodium alginate and sodium periodate in ethanol) in a sodium biphosphate-sodium citrate buffer of pH 8.4, followed by a solution of the second enzyme 110. Unbound enzymes are washed away by PBS buffer of pH 7.4 and the area is treated with a sodium cyanoborohydride solution. Accordingly, the first and second enzymes 106, 110 are properly immobilized on the substrate 104.

To facilitate the measurement of the target enzyme in either direct or indirect manner, the system, in an embodiment, further has a third enzyme immobilized on the same or different substrate via a third linker. The third linker contains a polymer, a peptide or an amino acid sequence which is preferably cleavable by the first enzyme to release the associated third enzyme. The third enzyme is different from the first and second enzymes and can subsequently trigger a chromogenic reaction upon release. Advantageously, the chromogenic reaction between the third enzyme and a chromogenic substrate in the reaction mixture produces signals reflecting the amount of the target enzyme in the sample.

Figure 3:
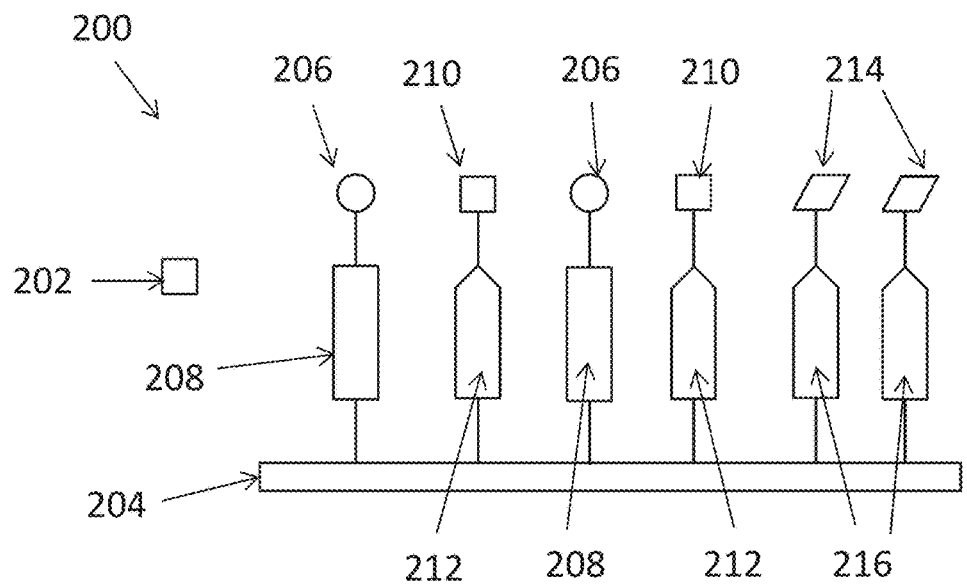
FIG. 3 is a diagram showing a system of another embodiment of the present invention.

FIG. 3 illustrates a system 200 for detecting the target enzyme 202. The system 200 has the first enzyme 206 and the second enzyme 210 immobilized separately on the substrate 204 via the first linker 208 and the second linker 212. The first and second enzymes 206, 210 are as described above, i.e. the same or similar to the first and second enzyme 106, 110. The system 200 further has a third enzyme 214 immobilized on the same substrate 204 via a third linker 216. The third linker 216 has a cleavage site similar to or the same as that in the second linker 212 so as to be cleaved by the same enzyme, i.e. the first enzyme 206. The third linker 216 may therefore be substantially identical or identical to the second linker 212. For example, when the second linker 212 includes an alginate moiety providing a cleavage site for alginate lyase, the third linker 216 also includes an alginate moiety. For illustrative purposes, the third linker 216 shares the same symbol with the second linker 212 in FIG. 3.

All the first, second and third linkers 208, 212, 216 are coupled onto the surface of the substrate 204 in a similar manner as discussed before.

When a sample containing the target enzyme 202 is introduced to the system 200, the target enzyme 202 contacts the substrate 204 particularly any first linker 208 on the substrate 204. The target enzyme 202 triggers the chain of enzymatic reaction by cleaving the first linker 208 to release the first enzyme 206. The first enzyme 206 then cleaves the second linker 212 and the third linker 216 to respectively release the second enzyme 210 for amplification and the third enzyme 214 for subsequent colorimetric analysis.

Preferably, after introducing the sample to the system 200, the system is allowed to react for a period of time before conducting any quantitative or qualitative measurements. At least a portion of, or a measured portion of. the resultant mixture in the system 200 containing the released third enzyme 214 may then be transferred into a mixture containing a chemical substance reactive with the third enzyme 214 for determining the presence and/or amount of the third enzyme 214.

In an embodiment, the chemical substance may be one or more chromogenic reagents and/or substrates specific to the third enzyme 214 for reaction to give colour for colorimetric detection. Chromogenic substrates may be any substances that can react with the third enzyme 214 to produce a colourimetric response. For example, the chromogenic substrates may be peptides that react with proteolytic enzymes under the formation of colour, attached to the peptide part is a chemical group which when released after the enzyme cleavage give rise to colour.

In an embodiment where the third enzyme 214 is horseradish peroxidase, the mixture may contain 3,3',5,5'-tetramethylbenzidine (TMB) as the chromogenic substrate and hydrogen peroxide as a oxidizing agent. The released third enzyme 214 catalyzes the oxidation of TMB and the resultant oxidized TMB (denoted as oxTMB) changes the colour of the entire reaction mixture. The light absorbance of the resultant reaction mixture can then be determined by using a colorimeter. With reference to a standard curve of light absorbance using known concentrations of the target enzyme, a user can easily find out the unknown concentration of the target enzyme in the sample. It would be appreciated that the detection of the target enzyme in the sample is conducted under the same conditions used in generating the standard curve.

In another embodiment, the third enzyme may be replaced by a luminophore or an electroactive molecule to give a signal for detection. For example, when the luminophore or the electroactive molecule is released from the substrate, the associated changes in luminescence or reduction-oxidation properties of the resultant mixture in the system 200 can be measured by various appropriate approaches.

Figure 4:
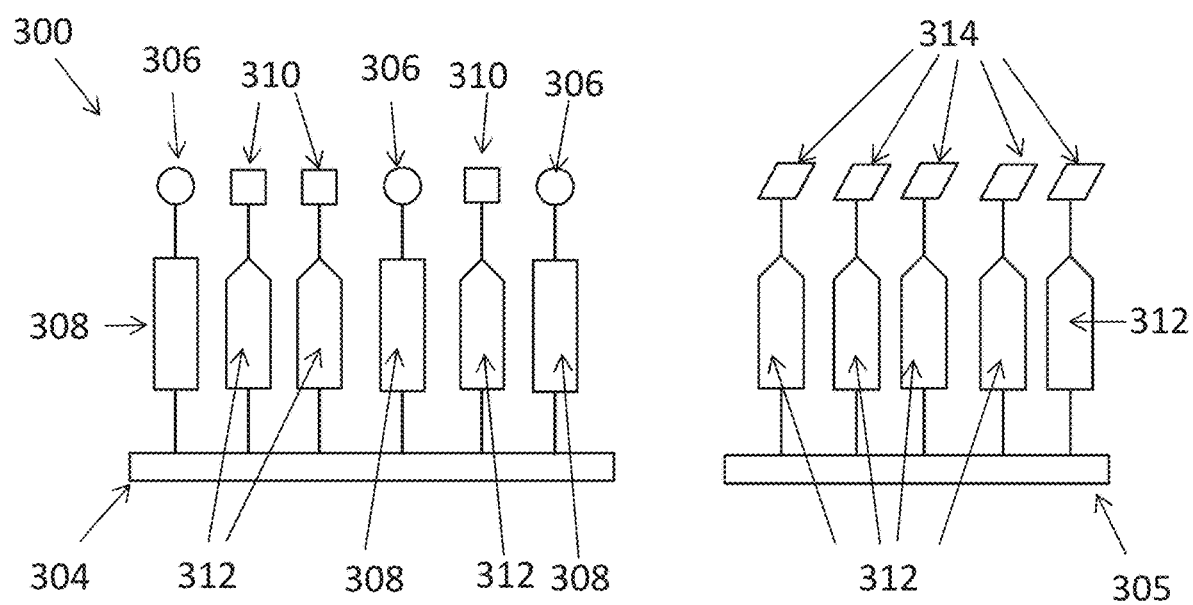
FIG. 4 is a diagram showing a system of a further embodiment of the present invention.

Further, it would be appreciated that the first, second and third enzymes of the present invention may or may not be immobilized on the same substrate. They can be provided in different combination on the same or different substrate. In a system 300 as shown in FIG. 4, the first and second enzymes 306, 310 are immobilized on the same substrate 304 via the first and second linker 308, 312, whilst the third enzyme 314 is immobilized on a separate substrate 305 via the third linker. The third linker is identical to the second linker 312 and therefore denoted with the same numeral reference. The substrates 304, 305 can be placed in the same reaction chamber for simultaneously reactions or in separate reaction chambers for sequential reactions. In a particular embodiment, the substrates 304, 305 are placed in a single reaction chamber.

The sample and the substrates 304, 305 are incubated for a period of time. The incubation may be performed at about 20° C. to 45° C., about 30° C. to 40° C., or about 37° C. for at least 15 min, about 30 min, about 45 min, or about 1 h. After incubation, a user can transfer the reaction mixture, e.g. or a supernatant of the reaction mixture, to a separate reaction zone/chamber for colorimetric analysis by using a mixture containing a chromogenic substrate as described above.

The one or more substrates immobilized with the first, second and/or third enzyme as described above can be provided in a kit for a user to operate. The kit may further contain a mixture containing a chromogenic substrate and optionally an oxidizing agent for colorimetric analysis after incubating the sample and the one or more substrates for a period of time. It would be appreciated that an manual may be provided in the kit guiding a user.

Accordingly, there is also provided a method of preparing the substrate as described above, i.e. a substrate immobilized with first, second and/or third enzymes via different linkers as described above. Preferably, the method comprises the following steps:
  (i) providing a substrate optionally having a binding group exposed on its surface;
  (ii) immobilizing a first enzyme on the substrate via a first linker, and immobilizing a second enzyme on the substrate via a second linker, wherein the first linker is cleavable by the target enzyme or the second enzyme to release the first enzyme for cleaving the second linker.

For step (i), the substrate may be modified by an acid and an oxidizing agent to carry amino groups on its surface. Amino groups are suitable for linkers having a polysaccharide or an amino acid sequence. The presence of the amino groups on the substrate facilitates the linkage between the linker and the substrate, thereby fixing the corresponding enzyme firmly on the substrate. In an embodiment, the substrate is pretreated with a strong oxidizing agent particularly a piranha solution for a period of time under sonication, and optionally rinsed with a buffer solution.

For the step (ii), the first and second enzymes are as described above and may be respectively coupled to the first and second linker before or after the immobilization step. The step (ii) may include fixing the first and second linker on the same or different substrate before coupling respectively with the first and second enzymes.

The method may further comprise a step (iii) of immobilizing a third enzyme on the same or different substrate via a third linker, wherein the third linker is cleavable by the first enzyme. The third enzyme and third linker are as described above. Preferably, the third linker is substantially identical or identical to the second linker.

In another aspect, there is provided a method of detecting a target enzyme in a sample comprising applying the sample to the system or on the substrate as described above. The system comprises a substrate having a first enzyme immobilized on the substrate via a first linker, and a second enzyme immobilized on the substrate via a second linker, wherein the first linker is cleavable by the target enzyme or the second enzyme to release the first enzyme for cleaving the second linker, thereby releasing the second enzyme.

The sample is preferably in liquid form and to be deposited on the surface of the substrate. The method then comprises a step of incubating the substrate at about 20° C. to 45° C. for at least 15 min to obtain a reaction mixture. Preferably, the incubation may be performed at about 30° C. to 40° C., or about 37° C. for at least 15 min, about 30 min, about 45 min, or about 1 h.

The method further comprises a step of subjecting at least a portion of the reaction mixture, or a supernatant of the reaction mixture, obtained after incubation to a colorimetric analysis. The colorimetric analysis involves a chromogenic substrate and includes the following steps of
  (a) transferring at least a portion of the reaction mixture or a supernatant of the reaction mixture to a reaction chamber, adding a mixture containing a chromogenic substrate as described above to the reaction chamber for chromogenic reaction;
  (b) quenching the chromogenic reaction by adding a quenching agent; and
  (c) measuring a light absorbance of the mixture obtained in step (b).

After step (c), the amount of the target enzyme in the sample can be determined with reference to a standard curve prepared by known concentrations of the target enzyme. The method herein is cost-effective and efficient approach for identification and detection of extracellular enzymes particularly extracellular proteases secreted by pathogens. It is applicable for clinical laboratory tests and diagnosis.

The examples set out below further illustrate the present invention. The preferred embodiments described above as well as examples given below represent preferred or exemplary embodiments and a skilled person will understand that the reference to those embodiments or examples is not intended to be limiting.

Example 1

Immobilization of Enzymes on Glass Slides

Figure 5:
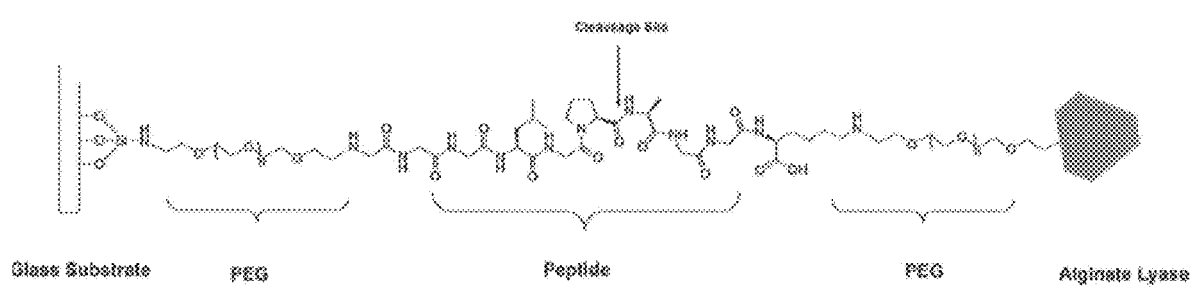
FIG. 5 is a schematic diagram showing an example of the first linker holding a first enzyme on the surface of the substrate, in which the first linker contains an amino acid sequence of SEQ ID NO:1 and connects to an alginate lyase.

To detect the presence or amount of collagenase in a sample, glass slides were first ultrasonic treated with piranha solution and APTES to form a surface rich in amino groups. As shown in FIG. 5, a peptide linker containing an amino acid sequence of $NH_2$-GGGLGPAGGK-$NH_2$, i.e. $NH_2$-SEQ ID NO: 1-$NH_2$, was coupled to a glass slide with one of its end being coupled with an alginate lyase. The target collagenase in the sample is capable of cleaving the peptide linker at the cleavage site, i.e. between leucine (L) and glycine (G), to release the alginate lyase. Polyethylene glycol (PEG) acts a bridge between the amino group on the glass slide and the peptide linker, as well as a bridge between the peptide linker and the alginate lyase.

Figure 6:
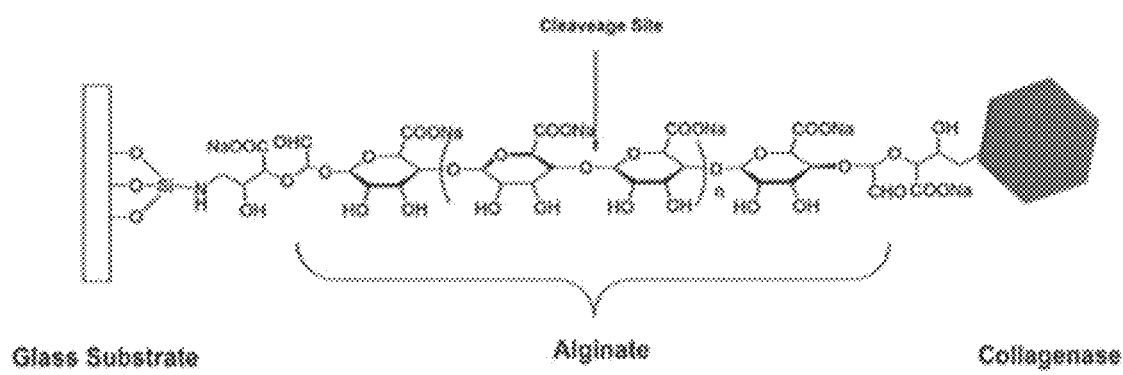
FIG. 6 is a schematic diagram showing an example of the second linker holding a second enzyme on the surface of the substrate, in which the second linker contains an alginate moiety and connects to a collagenase.

For another glass slide, as shown in FIG. 6, an alginate linker was used to immobilize a collagenase. Alginate polysaccharide was first oxidized to provide terminal aldehyde functional groups so as to couple with the amino groups formed on the surface of the glass slides. The alginate linker can be hydrolyzed by alginate lyase through breaking the glycosidic bond between β-D-mannuronate and α-L-guluronate units.

When the sample contains proteases particularly collagenases, they will cut the peptide linker in FIG. 5 to release alginate lyases. Alginate lyases will continuously cleave the alginate linker to free more collagenases. Accordingly, it forms a cleavage loop, and a small amount of collagenases in the sample is sufficient to trigger the loop. An increased amount of alginate lyases and collagenases will be released.

Another enzyme, horseradish peroxidase (HRP), was immobilized on a separate glass slide via an alginate linker in FIG. 6. The HRP will be released by the alginate lyases initially fixed by the peptide linker as shown in FIG. 5. The free or the released HRP can be transferred to a reading well that contains hydrogen peroxide and a chromogenic substrate TMB as HRP catalyzes TMB to give a high contrast colorless-to-blue colour change for detection.

Example 2

Preparation of Standard Curve

The glass slides prepared in Example 1 were placed in a well for reaction. In particular, the glass slides immobilized with alginate lyases, collagenases and HRP were fixed in a 12-well microplate (with inner diameter of 2.4 cm) for the autocatalytic amplification loop.

To prepare a standard curve, collagenase with different known concentration was applied to the well for triggering the amplification loop. After 30 mins of incubation, 50 µL of the supernatant solution was obtained from the well and transferred in to a new well. 50 µL TMB substrate was added to the new well for chromogenic reaction. After 5 mins of incubation at 37° C., 20 µL of 2 M HCL containing 20 mM $NaHSO_3$ was added to quench the reaction. The resultant mixture was then transferred into a cuvette for measuring the light absorbance at 450 nm. The oxidized TMB (denoted as oxTMB) is the product of the chromogenic reaction which gives colour for measurement. A microplate reader was adopted for the measurement.

Figure 7:
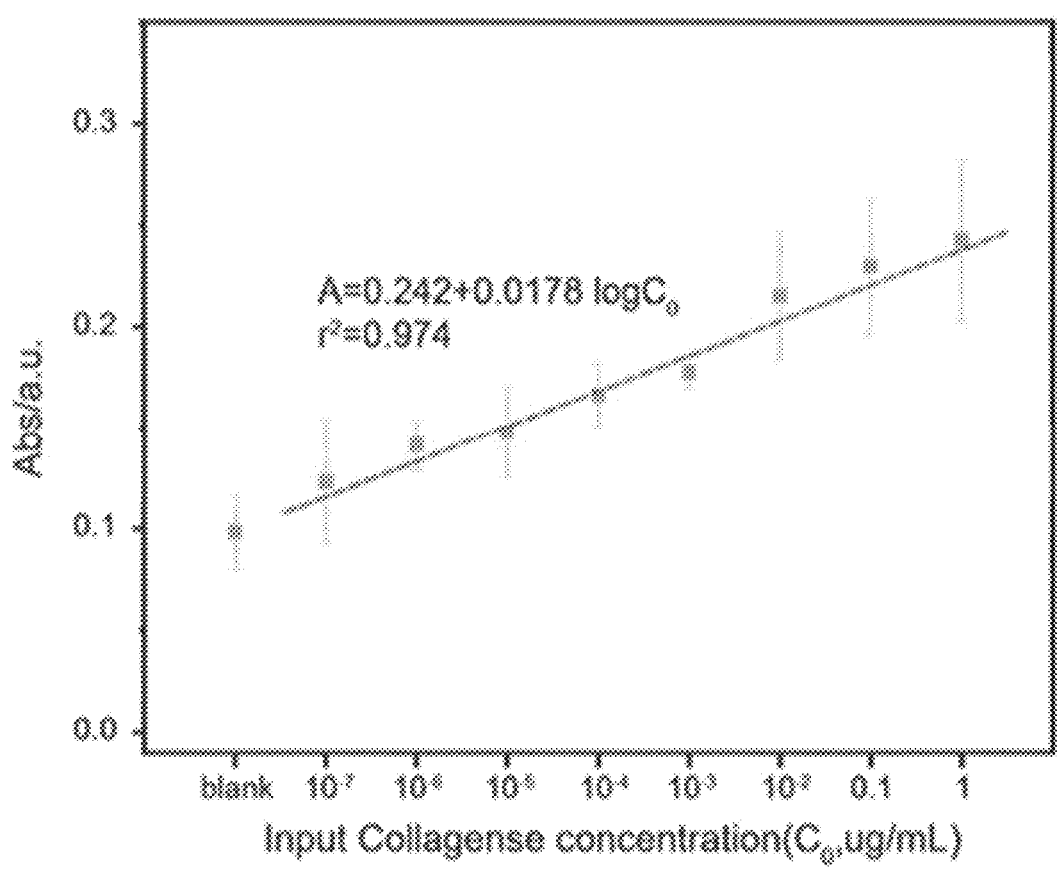
FIG. 7 is a plot of light absorbance vs concentration of collagenase prepared by using standard solutions of collagenase.

The results are represented in FIG. 7 which shows the oxTMB responses of the system utilizing three enzymes against various concentrations of target collagenases. The results prove that the system of the present invention is effective to detect a target enzyme for example extracellular proteases at low limitation limit. From the figure, the sensing signal bears good linear relationship with log-concentration of collagenase over the range from $10^{-5}$ to 1 µg mL$^{-1}$. The results demonstrate that the detection limit of the system can be as low as 11 pg/mL which is calculated based on the mean value of the background signals plus three times standard deviation of the background signals.

Example 3

Detection of Extracellular Collagenases in Bacterial Culture

To further determine whether the system is suitable for detection of bacteria in a culture medium, the inventors incubated an *E. coli* culture. Supernatants of the *E. coli* culture obtained after serial dilution were subjected to the system of the present invention, particularly the one as prepared according to Example 1 and 2.

Figure 8:
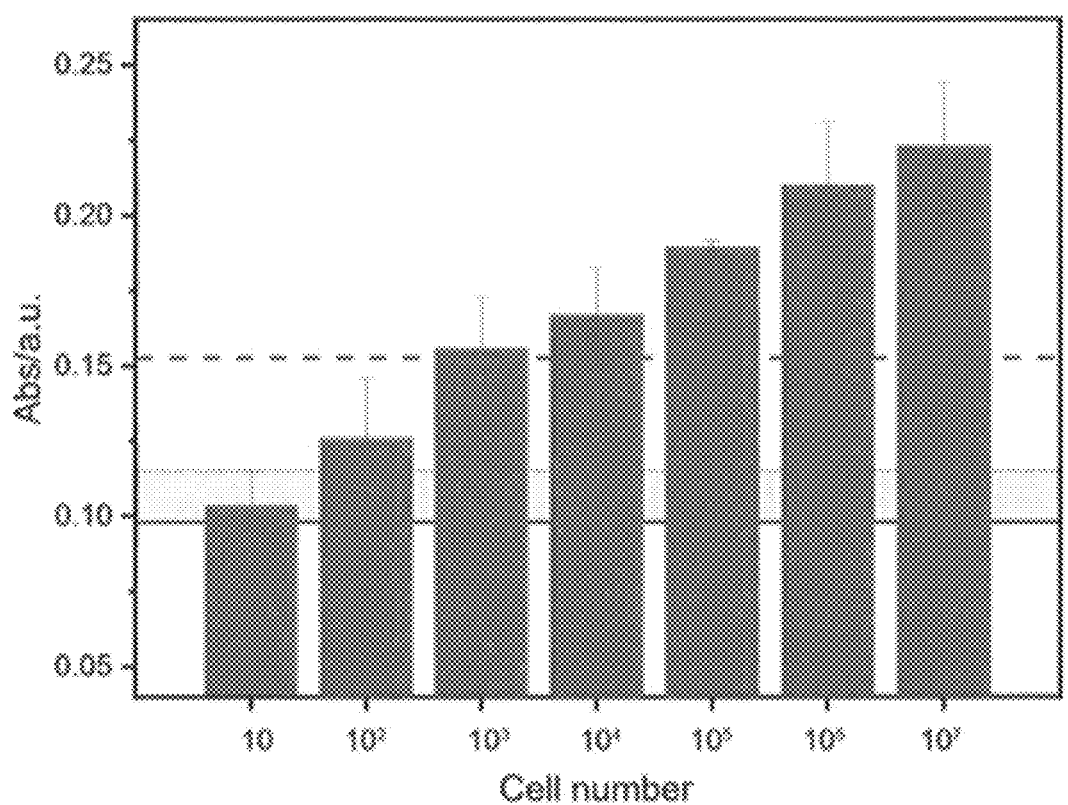
FIG. 8 is a bar chart of light absorbance vs cell number of *E. coli* in a culture solution.

FIG. 8 depicts the oxTMB signal output of the system showing that the level of extracellular collagenase from as slow as $10^3$ CFU of *E. coli* can be readily detected by the system. The solid line is the average background signal; the dash line is the average background signal plus standard deviation of the background signals and the dot line is the average background signal plus three times of the standard variation. The results demonstrate that the system is applicable to detect bacteria contamination in food products.

It would be appreciated that the linkers and the enzymes immobilized on the substrate of the present invention can be modified according to the structure and character of the target enzyme. For example, the cleavage site of the linker can be modified with other functional moieties so as to be cleaved by the target enzyme to trigger the amplification loop.

Since numerous species-specific extracellular proteases of pathogens are their virulent factors, the system herein is suitable for the culture-independent diagnostics of pathogens in patient's body fluids or in food samples. The system herein significantly improves the turnaround time for pathogen identification in clinical laboratories, e.g. from 24-48 hr to 30 min.

Example 4

Duo-Enzymes Systems

The inventors further tested the efficiency of utilizing a system having two enzymes in detection of a target enzyme. Separate experiments were conducted using either immobilized alginate lyase or collagenases as described in Example 1, along with the immobilized HRP in the system.

Figure 9:
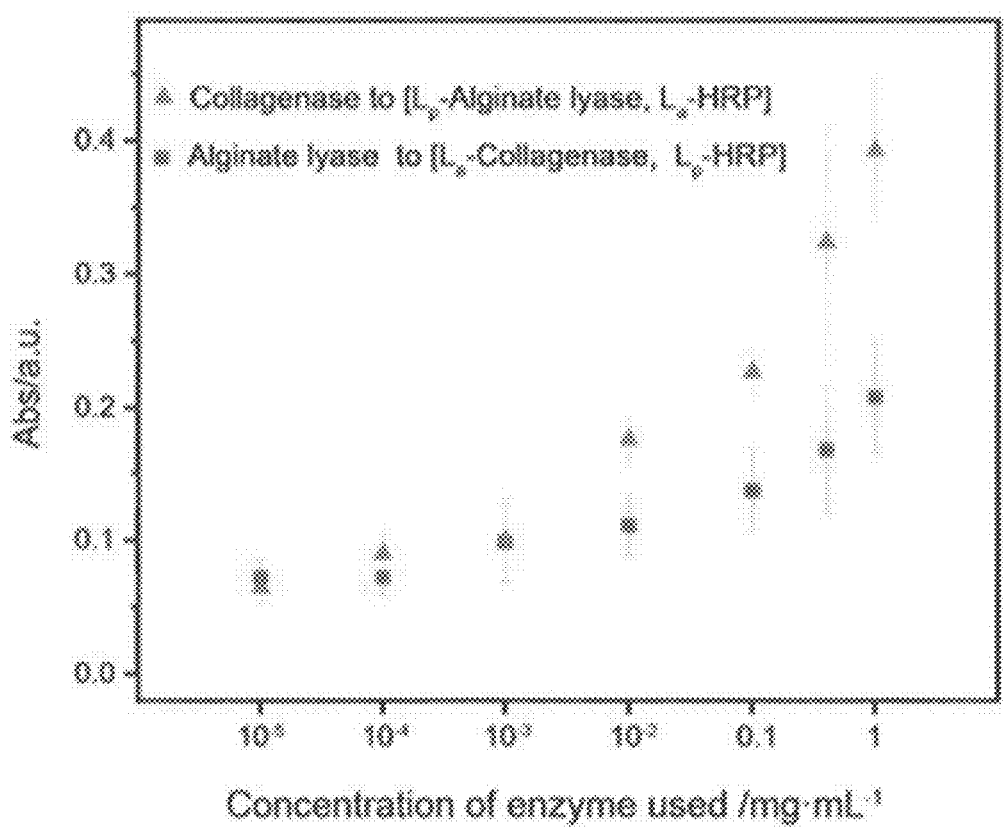
FIG. 9 is a plot of light absorbance vs concentration of enzyme obtained from a comparative experiment, in which the experiment compares the results obtained from two different systems.

FIG. 9 shows the oxTMB signals from the two duo-enzymes systems, one involved immobilized alginate lyase and immobilized HRP (results denoted with triangles) and another one involved immobilized collagenase and immobilized HRP (results denoted with squares). The results show that the two systems can also detect the presence or amount of the target enzyme when the target enzyme is at a concentration of $10^{-2}$ or above, particularly 0.1 mg·mL$^{-1}$ or above, while the three-enzyme system as described in Example 2 has a higher efficiency and a lower detection limit.

It will be appreciated by persons skilled in the art that numerous variations and/or modifications may be made to the invention as shown in the specific embodiments without departing from the scope of the invention as broadly described. The described embodiments of the invention should therefore be considered in all respects as illustrative, not restrictive. Any reference to prior art contained herein is not to be taken as an admission that the information is common general knowledge, unless otherwise indicated.

The invention claimed is:

1. A system for detecting a target enzyme in a sample by way of an amplification loop, comprising: a substrate, a first enzyme comprising alginate lyase immobilized on the substrate via a first linker, and a second enzyme comprising collagenase immobilized on the substrate via a second linker;
wherein the amplification loop is triggered by the target enzyme upon cleaving the first linker to release the first enzyme for cleaving the second linker, thereby releasing the second enzyme, and wherein the released second enzyme has a structure that allows it to cleave the first linker to release more of the first enzymes for continuously triggering the enzymatic cleavage reaction on the substrate.

2. The system of claim 1 further comprises a third enzyme immobilized on the same or different substrate via a third linker, wherein the third linker is cleavable by the first enzyme.

3. The system of claim 2, wherein the third linker is substantially identical to the second linker.

4. The system of claim 2, wherein the third enzyme is reactive with a chromogenic substrate to give colour for colorimetric detection.

5. The system of claim 4, wherein the chromogenic substrate is 3,3',5,5'-tetramethylbenzidine.

6. The system of claim 2, wherein the third enzyme is horseradish peroxidase.

7. The system of claim 2, wherein the third enzyme is linked with a luminophore or an electroactive moiety to give a signal for detection.

8. The system of claim 1, wherein the first linker comprises an amino acid sequence of SEQ ID NO: 1.

9. The system of claim 1, wherein the second linker comprises an alginate moiety cleavable by the first enzyme.

10. The system of claim 1, wherein the second enzyme is substantially identical to the target enzyme.

11. The system of claim 1, wherein the target enzyme is an extracellular protease.

12. The system of claim 11, wherein the target enzyme is collagenase.

13. A method for detecting a target enzyme in a sample comprising applying the sample to the system of claim 1.

14. The method of claim 13, wherein the system further comprises a third enzyme immobilized on the same or different substrate via a third linker, wherein the third linker is cleavable by the first enzyme.

15. The method of claim 14, wherein the third linker is substantially identical to the second linker.

16. The method of claim 14, wherein the third enzyme is reactive with a chromogenic substrate to give colour for colorimetric analysis.

17. The method of claim 14, wherein the third enzyme is horseradish peroxidase and the chromogenic substrate is 3,3',5,5'-tetramethylbenzidine.

18. The method of claim 14 further comprises a step of subjecting the reaction mixture, or a supernatant of the reaction mixture, obtained after incubation to a colorimetric analysis.

19. The method of claim 13, wherein the first linker comprises an amino acid sequence of SEQ ID NO: 1.

20. The method of claim 13, wherein the target enzyme is collagenase.

21. The method of claim 13 further comprises a step of incubating the substrate at about 20° C. to 45° C. for at least 15 min to obtain a reaction mixture.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Gly Gly Gly Leu Gly Pro Ala Gly Gly Lys
1               5                   10
```